United States Patent [19]
Konno et al.

[11] Patent Number: 5,318,035
[45] Date of Patent: Jun. 7, 1994

[54] CROSSLINKED MOLDING, SOUND MEDIUM USING IT AND ULTRASONIC COUPLER

[75] Inventors: Masayuki Konno; Fumiya Shirai; Hideo Sato; Tetsuo Horiuchi; Mitsuru Konno; Yuichi Inoue, all of Osaka, Japan

[73] Assignee: Nitto Denko Corporation, Osaka

[21] Appl. No.: 983,713

[22] Filed: Dec. 1, 1992

[30]  Foreign Application Priority Data

| Dec. 2, 1991 | [JP] | Japan | 3-347908 |
| Mar. 31, 1992 | [JP] | Japan | 4-77853 |
| Jun. 18, 1992 | [JP] | Japan | 4-186217 |
| Oct. 12, 1992 | [JP] | Japan | 4-272765 |
| Oct. 12, 1992 | [JP] | Japan | 4-272766 |
| Oct. 12, 1992 | [JP] | Japan | 4-272767 |

[51] Int. Cl.$^5$ ............................................ A61B 8/00
[52] U.S. Cl. ............................ 128/662.03; 264/240; 264/DIG. 42
[58] Field of Search ............ 128/662.03; 73/644; 264/85, 240, 272.16, DIG. 42

[56]  References Cited

U.S. PATENT DOCUMENTS

| 4,901,729 | 2/1990 | Saitoh et al. | 128/662.03 |
| 5,039,774 | 8/1991 | Shikinomi et al. | 128/662.03 |
| 5,078,149 | 1/1992 | Katsumato et al. | 128/662.03 |

OTHER PUBLICATIONS

"Acoustic Coupler", Hayabawa et al, Europ. Pat. WO90/01902 published Mar. 8, 1990.

*Primary Examiner*—Francis Jaworski
*Attorney, Agent, or Firm*—Sughrue, Mion, Zinn, Macpeak & Seas

[57]  ABSTRACT

A crosslinked molding, a process for producing the same, a sound medium using the same, and an ultrasonic coupler using the same are disclosed. The crosslinked molding comprises a crosslinked molding comprising a composition containing a rubbery elastic body comprising a hydrophobic high molecular weight material having at least one double bond in the molecule and an oily component dissolving the rubbery elastic body, the composition being crosslinked by the addition of an organic peroxide or by the irradiation of a radiation and molded.

20 Claims, 4 Drawing Sheets

CROSSLINKED MOLDING, SOUND MEDIUM USING IT AND ULTRASONIC COUPLER

FIELD OF THE INVENION

The present invention relates to a crosslinked molding, a sound medium using the molding, and an ultrasonic coupler used in carrying out an image diagnosis in a living body, a fresh diagnosis of domestic animals, or a medical treatment utilizing ultrasonic waves.

BACKGROUND OF THE INVENTION

Hitherto, a rubber polymer containing an oily component is subjected to a crosslinking treatment to provide a so-called oily gelatinous material as described in, e.g., JP-B-54-2661, JP-B-54-4734, and JP-B-2-61496 (the term "JP-B" as used herein means an "examined published Japanese patent application"), and a gelatinous material is obtained by subjecting a rubbery polymer containing water and a water-soluble plasticizer to a crosslinking treatment as described in, e.g., JP-A-2-71731 (the term "JP-A" as used herein means an "unexamined published Japanese patent application").

Since such gelatinous materials are usually excellent in shape retention property, flexibility, elasticity, low-temperature insulation property, etc., they are used as a stress dispersing material such as a mat for preventing a mattress injury, arresting sound, a vibration prevention, a head cooling belt, a cooling pillow, etc. Also, recently, by utilizing the sound characteristics of these gelatinous materials, they are utilized for an ultrasonic transmitting medium (sound medium), etc., and development of them for various products have been expected.

In the development of the uses of the gelatinous materials, a means for using an ultrasonic diagnosis apparatus for diagnosing the abnormality of the tissue on the inside of a living body and the pulsation of a bleed stream has been actively practiced as a sound medium. In such an ultrasonic diagnosis, ultrasonic pulses generated from a diagnosis apparatus are applied to the inside of a testee through an ultrasonic probe which is in close contact with the surface of the living body of the testee and waves reflected from the inside of the testee are detected. In this case, if the contact of the probe and the surface of the living body is insufficient and an air layer exists between them at the diagnosis, the applied ultrasonic waves greatly attenuate and a correct diagnosis cannot be made. Therefore, a method of improving the contact by coating the surface of the living body with an oily material such as an animal oil, a vegitable oil, paraffin, polyethylene glycol, etc., a pasty material, or a jelly-like material is usually employed.

However, the above method has problems, such as the surface of the testee becomes sticky and is stained to give an uncomfortable feeling, as well as since an oily material is liable to flow, the oily material cannot be uniformly coated, whereby the diagnosis result is liable to fluctuate. Also, in the case of diagnosing a site near the surface of a testee in an ultraviolet diagnosis, it is necessary to move the focus region of the ultrasonic pulse applied from the probe to the site diagnosed.

Accordingly, since a material which does not have a shape retaining property and is liable to flow, such as an oily material and a jelly-like material, is inferior in its handling properties, the development of a sound medium which has a shape retaining property and can freely change the thickness thereof has been desired.

As materials for solving these problems, gelatinous materials having a shape retaining property, flexibility, and proper elasticity are recently proposed as a sound medium for ultrasonic diagnosis. As such a medium, there are aqueous gels comprising aqueous polymeric materials and water as described in JP-A-59-82838, JP-A-1-146234, etc., and a polyurethane gel having liquid segments as the inside structure as described in JP-A-1-304109, etc.

However, although in the sound medium using the above-described gelatinous material, the disadvantages caused by the conventional oily materials, pasty material, and jelly-like material are overcome, in the case of the aqueous gel, since the gel contains water, there is a problem in custody that water contained in the aqueous gel is evaporated off and also the water content in the medium changes due to the influence of the humidity in the air to lose the flexibility. Also, in the case of the polyurethane gel, the material which can be used therefor is limited and a polyurethane gel useful for practical use has not yet been developed.

On the other hand, in the field of utilizing ultrasonic waves for ultrasonic medical treatment, ultrasonic waves are used for the treatment of chronic painful disease due to the pain-relieving effect, antiphlogistic effect, the effect of mitigating muscular cramp, etc., by applying ultrasonic waves onto the diseased part resulting in a temperature increase of the affected part, acceleration of the circulation at the affected part, acceleration of the permeability of the cell membrane, etc.

If the probe of an ultrasonic medical treatment device is not well contacted with the surface of the living body in the use of aiming such a medical treatment, the ultrasonic energy cannot be sufficiently applied into the body of a testee, whereby the various problems described above when using oily materials or pasty materials occur.

SUMMARY OF THE INVENTION

The present invention has been made to overcome the problems caused by conventional sound media.

One object of the present invention is to provide a crosslinked molding having shape retention property, flexibity, and a proper elasticity without being influenced with water, as well as having excellent sound characteristics.

Another object of the present invention is to provide a process of producing the crosslinked molding.

Still another object of the present invention is to provide a sound medium for carrying out an ultrasonic diagnosis and an ultrasonic medical treatment using the crosslinked molding.

A further object of the present invention is to provide a ultrasonic coupler using the crosslinked molding.

Thus, as the result of making various investigations for achieving the above objects, the inventors have discovered that not an aqueous gel containing water, but a specific oily gel component containing an oily material and showing restricted blooming has excellent shape retention property and sound characteristics and can achieve the above objects, and have succeeded in accomplishing the present invention.

According to one embodiment of the present invention, there is provided a crosslinked molding comprising a composition containing a rubbery elastic body comprising a hydrophobic high molecular weight material having a double bond in the molecule and an oily component capable of dissolving the rubbery elastic body, the composition being crosslinked by the addition with organic peroxide or by an irradiation of a radiation, and molded.

According to another embodiment of the present invention, there is provided a process of producing a crosslinked molding comprising the steps of:

(1) pouring a composition for forming a crosslinked molding containing a 1st rubber component comprising a hydrophobic high molecular weight material being compatible with an oily component and having at least one double bond in the molecule and an oily component, capable of dissolving the 1st rubber component in a mold having a definite form, or forming a film using the composition, (2) forming in layer form on the surface of an oil resistant plastic substrate a primer composition containing a synthetic resin component which is not dissolved in or swelled with an oily component and a 2nd rubber component comprising a hydrophobic high molecular weight material having at least one double bond in the molecule and compatible with the synthetic resin component, and (3) applying a crosslinking treatment to each composition in a state that the primer composition layer formed on the surface of the oil resistant plastic substrate is in contact with the surface of the composition for forming crosslinked molding injected in a mold or formed into a film.

According to still another embodiment of the present invention, there is provided a sound medium comprising the crosslinked molding used for ultrasonic diagnosis or ultrasonic medical treatment.

According to further embodiment of the present invention, there is provided an ultrasonic coupler having an ultrasonic probe-fixing member separably fixed to an ultrasonic probe and an oily gel composition layer connected to the fixing member, and existing between the transmitting and receiving wave plane of the ultrasonic probe and a testee, wherein a porous layer is formed at a part of the ultrasonic probe-fixing member and a sound medium comprising a crosslinked oily gel composition is formed on the inside and on the surface of the porous layer.

DETAILED DESCRIPTION OF THE INVENTION

Figure 1:
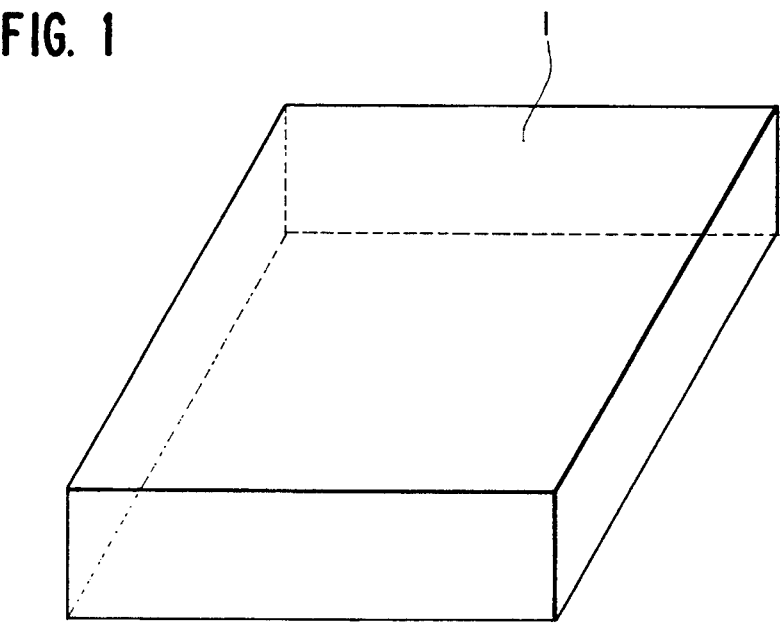
FIG. 1 is a slant view showing the crosslinked molding or the sound medium of the present invention.
Figure 2:
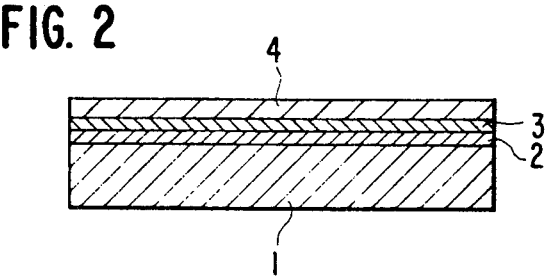
FIG. 2 is a cross-sectional view showing the crosslinked molding or the sound medium of another embodiment of the present invention.

The rubbery elastic body used in the present invention comprises a hydrophobic high molecular weight material having at least one double bond in the molecule and forms a crosslinked molding having a high elasticity, a shape retention property, and flexibility by being crosslinked in a state containing the oily omponent described hereinafter.

Examples of the hydrophobic high molecular weight materials are a natural rubber, a synthetic isoprene rubber, a butadiene rubber, a styrene-butadiene rubber, an acrylonitrile rubber, an acrylonitrile-butadiene rubber, a chloroprene rubber, a styrene-chloroprene rubber, an isobutyrene-isoprene rubber, a styrene-isoprene rubber, a styrene-butadiene-styrene rubber, a styrene-isoprene-styrene rubber, and an acrylic rubber.

Of these high molecular weight materials, a butadiene rubber, an isoprene rubber, and a styrene-butadiene rubber are particularly preferably used from the points of a high elasticity, a shape retention property, flexibility, and the stability of the material.

The double bond existing in the hydrophobic high molecular weight material causes a crosslinking reaction with an organic peroxide described hereinafter or causes a crosslinking reaction by irradiating the high molecular weight material with radiation to gel the high molecular weight material, whereby the hydrophobic high molecular weight material becomes a crosslinked molding having good elasticity and shape retention property.

In addition, the hydrophobic high molecular weight material used in the present invention means a high molecular weight material which is substantially insoluble in water and practically causes a weight increase of not more than 1.1% only of the original weight even when the high molecular weight material absorbs water.

Also, the addition amount of the oily component contained in the rubbery elastic body comprising the hydrophobic high molecular weight material can be optionally controlled according to the desired sound characteristics, gel strength (mechanical strength), modulus of elasticity, etc., but in the case of the present invention, for example, it is preferred that about 100 parts by weight of the oily component is added to from 3 to 150 parts by weight of the rubbery elastic body.

Specific examples of the oily component contained in the rubber elastic body are vegetable oils such as olive oil, castor oil, etc.; mineral oils such as fluid paraffin, process oil, etc.; ester oils such as diethyl sebacate, dioctyl phthalate, dioctyl adipate, ethyl cinnamate, ethyl phenylacetate, ethyl oleate, benzyl benzoate, etc.; animal oils such as squalane, squalene, etc.; and liquid emulsifying agents.

The sound characteristics of the sound medium of the present invention can be optionally changed according to the use purpose and in the case of using such for ultrasonic diagnosis or ultrasonic medical treatment, it is preferable that the sound characteristics fundamentally match the characteristics of water since the subject is a living body. That is, the sound characteristics are preferably adjusted such that the internal sound velocity of the sound medium near 20° C. becomes about 1,500 m/sec. and the sound impedance becomes about $1.5 \times 10^6$ kg/m$^2$·second. Also, the attenuation ratio differs according to the diagonostic site for ultrasonic diagnosis, but is preferably adjusted in the range of from about 0 to 3.0 dB/cm·MHz from the points of increasing the attenuation and reducing the multi echo, and also is preferably in the range of from 0 to 1.5 dB/cm·MHz for lowering the loss of the ultrasonic energy. Accordingly, in the sound medium of the present invention, it is suitable that the internal sound velocity at normal temperature is from 1,300 to 1,600 m/sec., the sound impedance is from 1.0 to $1.7 \times 10^6$ kg/m$^2$·second, and the attenuation is from 0 to 3.0 dB/cm·MHz.

The sound characteristics are influenced by the types of the rubbery elastic body and the oily component, and also the sound characteristics of each of them, but are liable to be particularly influenced by the type of the oily component uses. Accordingly, in the case of using the sound medium for ultrasonic diagnosis or ultrasonic medical treatment, it is preferable that the sound medium contains at least one kind of the oily components near the sound characteristics of a living body.

Since in a conventional oily component, the sound velocity is lower than the sound velocity in water and the attenuation of ultrasonic waves is relatively large, in ultrasonic diagnosis, a sound medium wherein the sound velocity is near the sound velocity in water and the attenuation of ultrasonic waves is near 0, which can be applied to a site such as an eyeball, etc., is difficult to obtain.

As the oily component dissolving the rubbery elastic body, which is one of the features of the present invention, dibasic acid esters such as diethyl sebacate, dibutyl sebacate, dioctyl adipate, etc., are preferable since these dibasic acid esters show less attenuation of ultrasonic pulses, are excellent in the solubility of the rubber elastic body, have a low solution viscosity after dissolving, and have a good workability. Also, the organic compounds having a benzene ring in the molecule and a specific gravity at 25° C. of at least 0.95, such as ethyl cinnamate, ethyl phenylacetate, benzyl benzoate, benzylbutyl phthalate, etc., are preferable since in these compounds, the internal sound velocity is near the sound velocity in water and the sound impedance is also near that of water.

In the present invention, a crosslinlked molding is obtained by crosslinking and gelling a composition containing the rubber elastic body and the oily material by incorporating therein an organic peroxide or by irradiating the composition with radiation.

Examples of the organic peroxide used for the crosslinking reaction in the former case are methyl ethyl ketone peroxide, cyclohexanone peroxide, cumene hydroperoxide, dicumyl peroxide, acetyl peroxide, lauroyl peroxide, benzoyl peroxide, t-butylperoxy-2-ethyl hexanoate, t-butylperoxy benzoate, peracetic acid, and a low molecular weight copolymer peroxide of a vinyl monomer and oxygen.

The organic peroxide is added in the range of from 0.05 to 40 parts by weight per 100 parts by weight of the rubbery elastic body. If necessary, a crosslinking reaction accelerator such as cobalt naphthenate, tin octenate, etc., can be added to the system in the crosslinking reaction.

On the other hand, as the radiation irradiating in the crosslinking reaction in the latter case, γ-rays or electron beams can be used and the dosage thereof is in the range of usually from 0.25 to 5.0 Mrad, and preferably from 0.5 to 3.0 Mrad.

If the dosage of the radiation is less than 0.25 Mrad, a crosslinked density capable of sufficiently keeping the gel strength is difficult to obtain, while if the radiation dosage is over 5.0 Mrad, the crosslinked density is too large, whereby the crosslinked molding obtained becomes hard, and in the case of applying the crosslinked molding to a skin surface as a sound medium, the contact with the skin surface is lowered and it sometimes happens that the oily component oozes.

It is preferable from the point of the crosslinking efficiency to usually apply a heating operation to the crosslinking and gelling under an oxygen-shield atmosphere (or an inert gas atmosphere).

Since the crosslinked molding and the sound medium of the present invention have been crosslinked and gelled by the addition of an organic peroxide or by the irradiation with radiation as described above, the oily component contained therein is not released as occured in the case of conventional crosslinked moldings, and hence does not stain during handling to give an uncomfortable feeling.

When the crosslinked molding of the present invention is used for ultrasonic diagnosis or ultrasonic medical treatment, an inorganic filler such as calcium carbonate, kaolin, silica, titanium oxide, etc.; glass beads; plastic beads such as polystyrene beads, methyl methacrylate beads, etc.; fibers such as Rayon fibers, polyester fibers, etc., can be properly compounded with the crosslinked molding to control the attenuation ratio of the ultrasonic pulses. Furthermore, since the crosslinked molding of the present invention contains the rubbery elastic body and the oily component, there is a possibility of causing heat deterioration, oxidation deterioration, light deterioration, etc., and hence it is preferable for preventing the occurrence of these deteriorations to add various kinds of antioxidants (age resistors) to the crosslinked molding. If necessary, various kinds of pigments, perfumes, tackifiers, various kinds of oily rubbers as gel strength increasing agents, etc., can be added to the crosslinked molding.

When the crosslinked molding and the sound medium of the present invention are placed as they are on a paper or a vinyl chloride sheet for a long period of time, there is a possibility that the oily component contained therein will transfer into the paper or the vinyl chloride sheet to stain or swell the sheet and hence after using them, it is necessary to place them in a definite case to prevent the transfer of the oily component. As a method of preventing the transfer of the oily component, a method of covering the surface of the oily gelatinous crosslinked molding or sound medium with an oil resistant plastic film such as a polyamide film or a polyurethane film is preferred at the point of handling.

As the covering method, there are a method of dissolving the material for the plastic film in a solvent and coating the solution on the surface of the crosslinked molding or the sound medium, followed by drying, and a method of covering the surface of the crosslinked molding or the sound medium with a plastic film which is formed separately. In the case of using the former method, it is necessary to use a solvent immiscible with the oily component. As the solvent used in this case, a mixed solvent of a lower alcohol and an organic solvent is preferred. As the oil resistant plastic film used, an alkoxymethylated polyamide film is particularly preferably used.

In the case of covering the surface of the crosslinked molding or the sound medium of the present invention with an oil resistant plastic film, in order to prevent the occurrence of abnormal pulse and ghost, it is necessary to completely and closely cover the surface such that air does not enter the covered surface. Accordingly, as a preferred covering method, there are a method of immersing the crosslinked molding or the sound medium in a solution of the oil resistant plastic and then drying, a method of coating the surface of the crosslinked molding or the sound medium with the solution of the oil resistant plastic one or more times and drying, and a method of spray coating the solution of the oil resistant plastic onto the surface of the crosslinked molding or the sound medium and drying.

The thickness of the oil resistant plastic layer thus formed is usually in the range of from 10 to 300 $\mu$m, and preferably from 20 to 150 $\mu$m, to avoid hindering the sound characteristics.

An example of producing the crosslinked molding as the sound medium of the present invention by crosslinking using an organic peroxide is described below.

First, the rubbery elastic body is dissolved in the oily component at room temperature or under heating, if necessary in an inert gas atmosphere, a definite amount of an organic peroxide is added to the solution thus formed at a temperature of not higher than the decomposition temperature of the peroxide, and after uniformly mixing them, a degassing treatment is carried out such that bubbles do not enter the solution.

If degassing is insufficient and bubbles remain in the solution, when the sound medium is formed from the solution, ultrasonic waves are scattered and absorbed by the bubbles in the medium to cause the attenuation of ultrasonic waves, whereby the image formed becomes indistinct and an abnormal pulse and ghosts undesirably form.

The solution subjected to the degassing treatment is poured in a frame of a definite form or formed into a film and the crosslinking treatment of the rubbery elastic body is carried out under an oxygen-free condition to gel the solution. The condition for the crosslinking treatment differs according to the kind of the rubbery elastic body and the kind and the amount of the organic peroxide used, but usually crosslinking is carried out in the temperature range of from 60° to 250° C. for from about 1 to 360 minutes.

The sound medium of the present invention thus obtained is used as it is or is used after cutting into a desired form after, if necessary, covering the surface thereof with an oil resistant plastic film.

On the other hand, in the case of carrying out crosslinking by irradiation with radiation, the solution subjected to the degassing treatment is prepared by the above-described method except that the organic peroxide is not added thereto, the solution is poured in a frame having a desired form, after sealing the pouring portion, the solution is irradiated with a radiation at a dosage of from 0.5 to 5.0 Mrad to carry out crosslinking to gel the solution.

By forming the crosslinked molding of the present invention on one surface of an oil resistant plastic substrate, the sticking work thereof to a member of fixing an ultrasonic probe can be improved. That is, by forming the crosslinked molding on one surface of the oil resistant plastic substrate and by forming an adhesive layer or a sticking agent layer on the other surface of the substrate, fixing to the member can be easily carried out.

However, since the oily gel-like crosslinked molding containing the oily component as in the present invention is reluctant to adhere onto the surface of an oil resistant plastic substrate, it is perferable to employ the method that after previously coating a primer composition comprising a specific synthetic resin component and a rubber component on the surface of the substrate to form the layer thereof, the composition for forming the crosslinked molding, which becomes an oily gel, is formed on the primer composition layer, and the crosslinking treatment is applied to each composition to cause the gelation in a body.

That is, the composition for forming the crosslinked molding containing the 1st rubber component comprising the hydrophobic high molecular weight material compatible with the oily component and having at least one double bond in the molecule and the oily component dissolving the 1st rubber component is poured in a mold having a definite form or formed into a film. Apart from this, a primer composition containing a synthetic resin component which is not dissolved in or not swelled with the oily component and a 2nd rubber component comprising a hydrophobic high molecular weight material having at least one double bond in the molecule and compatible with the synthetic resin component is previously formed in layer on the surface of an oil resistant plastic substrate.

Then, a crosslinking treatment is applied to each composition in a state that the primer composition layer formed on the surface of the oil resistant plastic substrate is in contact with the surface of the composition for the crosslinked molding poured in the mold or formed into a film.

As the 1st rubber component and the oily component used for the above-described method, the hydrophobic high molecular weight material and the oily component described above can be used.

The composition formed in layer on the surface of the oil resistant plastic substrate is for improving the affinity and the adhesive force for the substrate, the oily component, and the 1st rubber component, and such a primer composition contains a synthetic resin component which is not dissolved in or is not swelled with the oily component and a 2nd rubber component comprising a hydrophobic high molecular weight material having at least one double bond in the molecule and compatible with the synthetic resin component.

As the synthetic resin component, for example, an acrylic resin, an epoxy series resin, a polyamide series resin, a polyester series resin, a polyurethane series resin, and a phenol series resin can be used alone or as a mixture thereof.

These synthetic resin components have a function of increasing the affinity with the plastic substrate and it is preferred to use the synthetic resin having the same or similar to the plastic substrate from the point of adhhesive property. In this case, "the synthetic resin similar to the plastic substrate" means a synthetic resin having a skeleton which is similar to the skeleton of the main component constituting the plastic substrate (e.g., a synthetic resin having a same bond such as an ester bond, an ether bond, an amide bond, an urethane bond, etc., in the high molecular weight main chain as a repeating unit) or a synthetic resin having a solubility parameter (so-called SP value) similar to the SP value of the plastic substrate.

The 2nd rubber component contained in the primer composition together with the synthetic resin component is an important component for simultaneously causing a crosslinking reaction at crosslinking the adjacent composition for the crosslinked molding to strongly adhere both the compositions in a body. As such a 2nd rubber component, those illustrated above as the 1st rubber component can be used. The primer composition is coated on the oil resistant plastic substrate to form a layer having a thickness of about from 10 to 200 µm and hence a 2nd rubber component giving a good coating workability is preferred. From the point of such coating workability, as the 2nd rubber component, a so-called liquid rubber having a fluidity under a working temperature is preferably used from the point of a non-solvent coating property.

Examples of the liquid rubber used are a liquid butadiene rubber, a liquid isoprene rubber, a (meth)acrylated, maleated, or epoxidated modified liquid rubber, etc.

In addition, for improving the coating workability, the primer composition can, if necessary, contain an organic solvent such as toluene, methyl ethyl ketone, ethyl acetate, acetone, xylene, etc., for controlling the viscosity thereof.

As to the content ratio of the synthetic resin component and the 2nd rubber component in the primer composition, it is preferable that the content of the 2nd rubber component is from 10 to 100 parts by weight, and particularly from 15 to 40 parts by weight, per 100 parts by weight of the synthetic resin component. If the content of the synthetic resin component is too large, the adhesive property to the primer composition layer becomes inferior during crosslinking and gelling the composition for the crosslinked molding. On the other hand, if the content of the 2nd rubber component is too large, the adhesive property of the plastic substrate and the primer composition layer is reduced and also it sometimes happens that a large amount of the oily component transfers into the primer composition layer and the primer composition layer is peeled off from the substrate with the passage of time.

In the above production method, the composition for the crosslinked molding is first poured in a mold having a definite form or is formed into a film on a plane. On the other hand, the primer composition is coated in a layer on an oil resistant plastic substrate such as polyester, polystyrene, nylon, polymethyl methacrylate, polycarbonate, etc., to form a film and the film side (primer composition layer side) is contacted with the surface of the composition for the crosslinked molding poured in a mold having a definite form or formed into a film.

As another method of improving the adhesive strength between the oil resistant plastic substrate and the crosslinked molding than the above-described methods, there is a method of forming a porous layer at a part of the surface of the oil resistant plastic substrate and forming the crosslinked molding on the inside of the porous layer and on the surface thereof. That is, by crosslinking and gelling the composition for the crosslinked molding in a state that the porous layer is impregnated with the composition, the gel layer formed is in a state entering the porous layer to improve the adhesive strength.

Examples of the porous layer are a paper, a woven fabric, a nonwoven fabric, a net, a continuous foam, a plane fastener, etc. Of these materials, a woven fabric and a nonwoven fabric are preferred in the points of a mechanical stength, heat resistance, economy, etc. As the material for the woven fabric and the nonwoven fabric, a material which is not influenced by the oily component contained in the crosslinked molding is preferred and, there are, for example, polyester and nylon. The fabric having a basis weight of from 10 to 300 g/m$^2$, and preferably from 20 to 150 g/m$^2$ is preferable in the point of the impregnating property.

Figure 11:
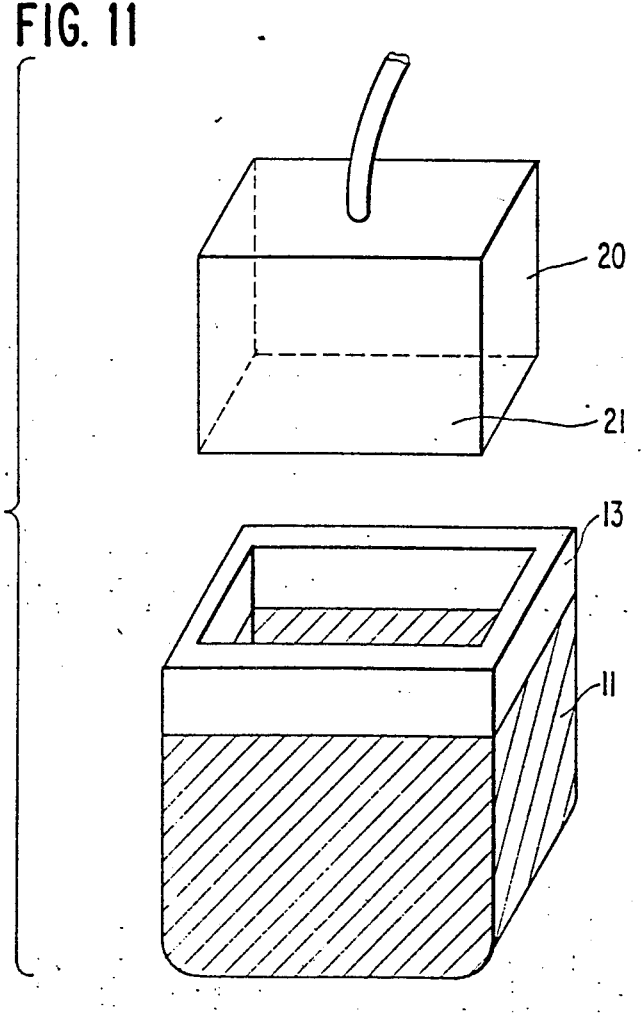
FIG. 11 is a view explaining a case of installing an ultrasonic probe to the ultrasonic coupler of the present invention.

In the case of using the crosslinked molding or the sound medium of the present invention as an ultrasonic coupler, as shown in FIG. 11, it is general that the ultrasonic coupler 11 is fixed to an ultrasonic probe-fixing member 13 in a body, the member 13 can be connected to or released from an ultrasonic probe 20, during a diagnosis or a medical treatment, the ultrasonic probe 20 is connected to the fixing member 13, and the ultrasonic coupler 11 is contacted with a testee to obtain a tomogram. In this case, for the ultrasonic probe-fixing member 13, a plastic molding such as a frame of the above-described oil resistant plastic substrate is used.

In the case of using as an ultrasonic coupler, there is a possibility that when the ultrasonic probe is connected and the ultrasonic coupler is moved on a testee in contact therewith, a shearing stress is applied to the inside of the sound medium comprising the crosslinked molding to rupture the medium, and hence it is preferred to use a reinforcing material. Such a reinforcing material is formed in contact with the crosslinked molding or a part or the whole of the reinforcing material is embedded in the crosslinked molding. As such a reinforcing material, a net, a plastic film, a paper, a nonwoven fabric, a woven fabric, etc., can be suitably used.

Figure 6:
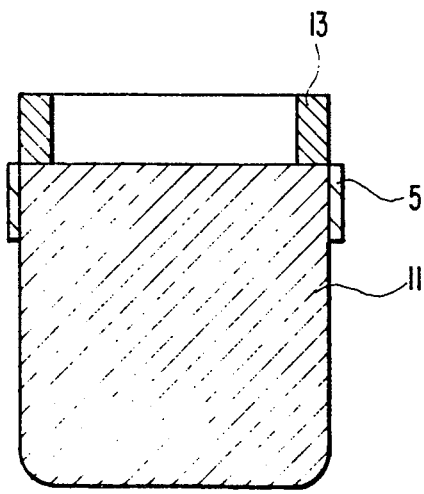
FIG. 6 is a cross-sectional view showing one example of the ultrasonic coupler of the present invention.
Figure 7:
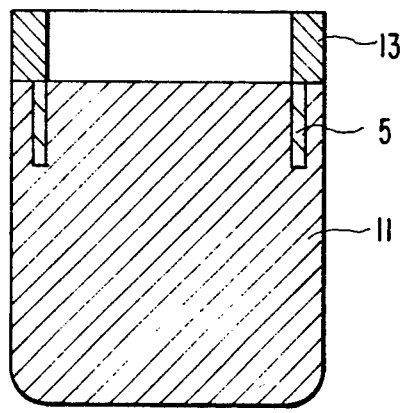
FIG. 7 is a cross-sectional view showing another examples of the ultrasonic coupler of the present invention.
Figure 8:
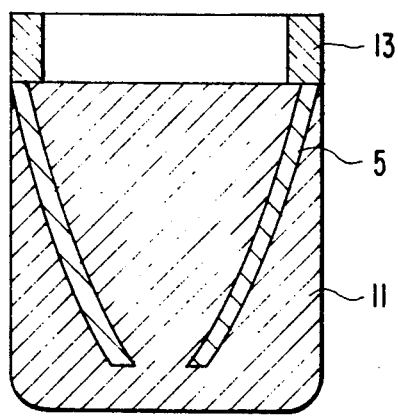
FIG. 8 is a cross-sectional view showing still another example of the ultrasonic coupler of the present invention.

As shown in FIG. 6 to FIG. 8, it is preferred that the reinforcing materials 5 are formed so as to avoid the progress of the ultrasonic pulses transmitted from the ultrasonic probe 20 and it is more preferred that the reinforcing materials 5 are formed in the perpendicular direction to the ultrasonic wave transmitting and receiving plane 21 (FIG. 11) as shown in FIG. 6 and FIG. 7. The constitution as shown in FIG. 7 or FIG. 8 can be obtained by immersing the reinforcing materials 5 in the solution of the composition for the crosslinked molding and thereafter crosslinking and gelling the composition.

Figure 9:
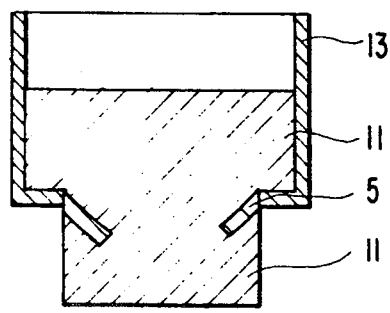
FIG. 9 is a cross-sectional view showing a further example of the ultrasonic coupler of the present invention.

On the other hand, when an ultrasonic coupler 11 has a brim-form portion and a fixing member 13 is disposed as wrapping the brim-form portion as shown in FIG. 9, it is preferred to dispose the reinforcing materials 5 at the positions shown in FIG. 9 for preventing the ultrasonic coupler 11 from being ruptured.

Figure 10:
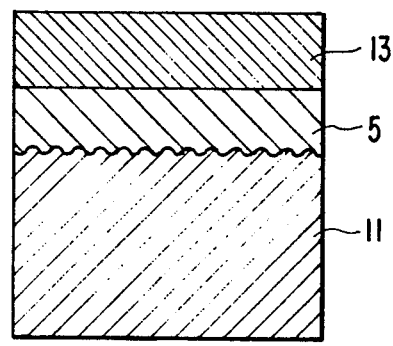
FIG. 10 is a cross-sectinal view showing still further example of the ultrasonic coupler of the present invention.

Furthermore, for improving the reinforcing effect, it is preferred to form holes in the reinforcing materials 5 or as shown in FIG. 10, to form uneven portions at the lower end of the reinforcing material 5 from the point of dispersing stress (for preventing the rupture of the gel).

The present invention is described more practically by the following examples.

EXAMPLE 1

After compounding 480 g of diethyl sebacate and 120 g of a styrene-butadiene rubber (styrene content:24 wt %, Mooney viscosity [ML 1+4, 100° C.]:32) while finely cutting the rubber, the mixture was heated to 100° C. with stirring under a nitrogen gas atmosphere to completely dissolve the rubber, thereby providing a viscous solution.

After cooling the viscous solution obtained to a temperature below 40° C., 2 g of pasty benzoyl peroxide (BPO content: 50% by weight, dispersion medium: dioctyl phthalate) was added to the solution, and after sufficiently stirring the mixture, the mixture was flow-cast in a mold (10 cm × 10 cm × 2 cm) followed by degassing.

After finishing the degassing treatment, the mixture was heat-treated at 120° C. for 2 hours under a nitrogen gas atmosphere to gel the viscous solution in the mold, thereby providing the crosslinked molding having the form shown in FIG. 1.

The gelatinous crosslinked molding obtained was flexible and had an elasticity. When the gel was immersed in water a whole day and night, the gel scarcely absorbed water, and when the gel was allowed to stand for 7 days at 60° C., the gel sufficiently kept the form and blooming of the oily component was not observed.

Furthermore, when the crosslinked molding was used for an ultrasonic coupler as the sound medium, the contact with the surface of a living body was very good and in the sound characteristics, the internal sound velocity was 1,394 m/sec., the sound impedance was $1.34 \times 10^6$ kg/$m^2$·second, and the attenuation ratio was 0.21 dB/cm·MHz.

When an ultrasonic diagnosis for the thyroid gland was carried out, a clear image having less multi-reflection was obtained.

EXAMPLE 2

After compounding 500 g of fluid paraffin and 60 g of an isoprene rubber (cis 1,4 bond:98%, Mooney viscosity [ML 1+4, 100° C.]:90) while finely cutting the rubber, the mixture was heated to 100° C. with stirring under a nitrogen gas atmosphere to completely dissolve the rubber and 25 g of calcium carbonate was then added to the solution followed by stirring sufficiently to provide a viscous solution.

After cooling the viscous solution obtained to a temperature below 40° C., 4 g of pasty lauroyl peroxide (the content and the dispersing medium were the same as those in Example 1) was added to the viscous solution and after sufficiently stirring the mixture, the crosslinked molding of the present invention was obtained using the mold as in Example 1.

The crosslinked molding obtained had almost the same properties as the product in Example 1. When the crosslinked molding was used for an ultrasonic coupler as the sound medium, the contact with the surface of a living body was very good and in the sound characteristics, the internal sound velocity was 1,396 m/sec, the sound impedance was $12 \times 10^6$ kg/$m^2$·second, and the attenuation ratio was 1.1 dB/cm·MHz.

When the crosslinked molding was used for an ultrasonic diagnosis, a clear image was obtained.

EXAMPLE 3

After compounding a mixture of 250 g of ethyl cinnamate and 250 g of ethyl phenylacetate with 100 g of a styrenebutadiene rubber (the same as in Example 1) while finely cutting the rubber, the mixture was heated to 100° C. with stirring under a nitrogen gas atmosphere to completely dissolve the rubber, thereby providing a viscous solution.

After cooling the viscous solution obtained to a temperature below 40° C., 9 g of pasty benzoyl peroxide (the same as in Example 1) was added to the viscous solution and after sufficiently stirring the mixture, the mixture was flow-cast in a mold (10 cm × 10 cm × 0.5 cm) followed by degassing. Thereafter, the surface of the solution was covered with a polyester film to shield air and the gelation treatment was carried out by the same manner as in Example 1 to provide the crosslinked molding of the present invention.

The crosslinked molding obtained had almost the same properties as the product in Example 1 and when the crosslinked molding was used as an ultrasonic coupler, the contact with the surface of the living body was very good. In the sound characteristics, the internal sound velocity was 1,476 m/second, the sound impedance was $1.45 \times 10^6$ kg/$m^2$·second, and the attenuation ratio was 0.24 dB/cm·MHz. When the product was used for an ultrasonic diagnosis, a clear image was obtained.

EXAMPLE 4

After immersing the sound medium obtained in Example 1 in an alkoxymethylated polyamide solution (solid component concentration:20% by weight, methanol/toluene=50/20% by weight), the sound medium was soon taken out from the solution and air-dried to provide a crosslinked molding having an oil resistant plastic film layer of 30 μm in thickness on the surface thereof.

The sound characteristics of the crosslinked molding were the same as those of the product in Example 1 and when the product was allowed to stand for 7 days at 40° C. on a paper or a polyvinyl chloride sheet, the transfer of the oily component was not observed.

EXAMPLE 5

The sound medium obtained in Example 2 was immersed in a polyurethane resin solution (solid component concentration: 20% by weight, toluene/ethyl acetate=50/20% by weight), the sound medium was soon taken out from the solution and air-dried to provide a crosslinked molding having an oil resistant plastic film layer of 50 μm in thickness on the surface thereof.

The sound characteristics of the crosslinked molding were almost the same as those in Example 2 and when the product was allowed to stand for 7 days at 40° C. on a paper or a polvinyl chloride sheet, the transfer of the oily component was not observed.

EXAMPLE 6

After cooling a viscous solution obtained by the same manner as in Example 1, the viscous solution was flow-cast in a mold as in Example 1 without adding an organic peroxide and a degassing treatment was carried out.

After finishing the degassing treatment, the viscous solution in the mold was irradiated with γ-ray of 2.0 Mrad to gel the solution to provide the crosslinked molding of the present invention.

The gelatinous crosslinked molding obtained was flexible and had an elasticity. When the gel was immersed in water a whole day and night, the gel scarcely absorbed water, and when the gel was allowed to stand for 7 days at 60° C., the gel sufficiently kept the shape and blooming of the oily material was not observed.

Furthermore, when the crosslinked molding was used for an ultrasonic coupler as the sound medium, the contact with the surface of a living body was very good and in the sound characteristics, the internal sound velocity was 1,394 m/sec., the sound impedance was 1.34×10⁶ kg/m²·second, and the attenuation ratio was 0.21 dB/cm·MHz. When the product was used for an ultrasonic diagonosis of the thyroid gland, a clear image having less multi-reflection was obtained.

EXAMPLE 7

After cooling the viscous solution obtained by the same manner as in Example 3 to a temperature below 40° C., the viscous solution was flow-cast in a mold as in Example 6 without adding an organic peroxide followed by degassing and the viscous solution in the mold was irradiated with γ-ray of 2.0 Mrad to gel the solution, thereby providing the crosslinked molding of the present invention.

The crosslinked molding obtained had almost the same properties as the product in Example 6 and when the product was used as an ultrasonic coupler, the contact with the surface of a living body was very good. In the sound characteristics, the internal sound velocity was 1,476 m/sec., the sound impedance was $1.45 \times 10^6$ kg/m²·second, and the attenuation ratio was 0.24 dB/cm·MHz, and a clear image was obtained.

EXAMPLE 8

After compounding a mixture of 250 g of dibutyl sebacate and 175 g of benzylbutyl phthalate with 100 g of a styrene-butadiene rubber (same as in Example 6) while finely cutting the rubber, the mixture was heated to 100° C. with stirring under a nitrogen gas atmosphere to completely dissolve the rubber, thereby providing a viscous solution.

After cooling the viscous solution obtained to a temperature below 40° C., the viscous solution was flow-cast in a mold (10 cm×10 cm×0.5 cm) followed by degassing, the surface of the solution was covered with a polyester film to shield air. The viscous solution in the mold was irradiated with γ-ray of 2.5 Mrad to gel the viscous solution in the mold, thereby providing the crosslinked molding of the present invention.

The crosslinked molding obtained had almost the same properties as the product in Example 6 and when the product was used as an ultrasonic coupler, the contact with the surface of a living body was very good. In the sound characteristics, the internal sound velocity was 1,440 m/sec., the sound impedance was $1.44 \times 10^6$ kg/m²·second, and the attenuation ratio was 0.45 dB/cm·MHz. Also, a clear image was obtained.

EXAMPLE 9

After cooling the viscous solution obtained by the same manner as in Example 2 to a temperature below 40° C., the viscous solution was flow-cast in a mold as in Example 6 without adding an organic peroxide followed by degassing and the viscous solution in the mold was irradiated with γ-ray as in Example 6 to gel the solution, thereby providing the crosslinked molding of the present invention.

The crosslinked molding obtained had almost the same properties as that in Example 6 and when the product was used as an ultrasonic coupler for an ultrasonic diagonisis of the mammary gland, the contact with the surface of a living body was very good. In the sound characteristics, the internal sound velocity was 1,396 m/sec., the sound impedance was $1.12 \times 10^6$ kg/m²·sec., and the attenuation was 1.1 dB/cm·MHz. Also, a clear image was obtained.

EXAMPLE 10

After immersing the sound medium obtained in Example 6 in an alkoxymethylated polyamide solution (solid component concentration:20% by weight, methanol/toluene=50/50% by weight), the sound medium was soon taken out and air-dried to provide a crosslinked molding having an oil resistant plastic film layer of 30 μm on the surface thereof.

The sound characteristics of the crosslinked molding were almost the same as those of the product in Example 6 and when the product was allowed to stand for 7 days at 40° C. on a paper or a soft polyvinyl chloride sheet, the transfer of the oily component was scarcely observed.

EXAMPLE 11

A viscous solution was prepared as in Example 1 and after adding thereto an organic peroxide as in Example 1, the mixture was flow-cast in a mold followed by degassing.

On the other hand, 50 g of a polyester resin was dissolved in a mixed solvent of toluene/methyl ethyl ketone (50/50% by weight) such that the solid component concentration became 30% by weight and 10 g of acrylated liquid polubutadiene was then added thereto to provide a uniform primer composition solution. The solution was coated on one surface of a polyester film of 25 μm in thickness and dried at 40° C. for 5 hours to evaporate off the solvent, thereby forming a primer composition layer of 50 μm in thickness.

Figure 3:
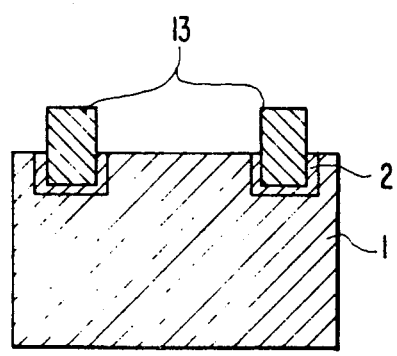
FIG. 3 is a cross-sectional view showing the crosslinked molding or the sound medium of still another embodiment of the present invention.

The surface of the composition for crosslinked molding degassed as described above was covered in contact with the primer composition layer formed on the surface of the substrate and the composition for crosslinked molding in the mold was crosslinked and gelled to integrate with the primer composition layer in one body. A double-sided adhesive tape having an acrylic adhesive layer on both surfaces thereof was stuck to the opposite surface of the substrate to provide a sheet-form crosslinked molding as shown in FIG. 3.

The crosslinked molding thus prepared showed no sticking property at the oily gel portion, was flexible and rich in elasticity. When the crosslinked molding was allowed to stand for 7 days at 60° C., the oily component (diethyl sebacate) in the gel did no transfer into the double-sided adhesive tape and had been strongly adhered to the polyester film which was the substrate. When the sheet-form crosslinked molding was adhered to a frame composed of an aluminum plate and observed for one month under normal conditions, it kept a good adhesive property.

EXAMPLE 12

A viscous solution was prepared by the same manner as in Example 2 and after adding thereto the organic peroxide, the mixture was flow-cast in a mold and degassed as in Example 2.

On the other hand, 50 g of a polyester resin was dissolved in a mixed solvent of toluene/methyl ethyl ketone (50/50% by weight) such that the solid component concentration became 30% by weight and 35 g of a methacrylated liquid polyisoprene rubber solution (solvent: toluene, solid component concentration: 20% by weight) to provide a uniform primer composition solution. The solution was coated on one surface of an acrylic resin plate of 5 mm in thickness and dried at 40° C. for 5 hours to evaporate off the solvent, thereby forming a primer composition layer of 60 μm in thickness.

The surface of the composition for crosslinked molding degassed above was covered in contact with the primer composition layer formed on the surfce of the substrate, the assembly was heat-treated at 100° C. to crosslink and gel the composition for crosslinked molding in the mold to integrate with the primer composition layer in one body, thereby providing the crosslinked molding shown in Table 3.

The crosslinked molding prepared could be used as an ultrasonic coupler for carrying out an image diagonosis utilizing ultrasonic waves and since the holder (the acrylic resin plate) for fixing an ultrasonic probe was integrated with the gel in one body, they could be easily handled. The gel charactersitics of the oily gel portion were almost the same as in Example 11 and showed excellent gel characteristics and a good adhesive property to the substrate.

EXAMPLE 13

A composition for crosslinked molding obtained by the same manner as in Example 12 was filled in a heat-sealable molding vessel and after carrying out a defoaming treatment, the composition was covered in contact with the primer composition layer formed on the surface of a polyester substrate.

The assembly was covered by a film for heat seal and after heat sealing the molding vessel, the composition for crosslinked molding in the vessel was irradiated with γ-ray of 2.5 Mrad to crosslink and gel the composition for crosslinked molding to integrate with the primer composition in one body, thereby providing a crosslinked molding.

The crosslinked molding thus prepared showed no adhesive property at the gel portion as in Example 12, was flexible and was rich in elasticity. When the product was allowed to stand for 7 days at 60° C., the product strongly adhered to the polyester substrate without being released therefrom.

COMPARATIVE EXAMPLE 1

A composition for crosslinked molding obtained by the same manner as in Example 11 was flow-cast in a mold, after carrying out a defoaming treatment, the surface of the composition for crosslinked molding was covered with a polyester substrate having no coating of a primer composition, and heat-treated at 120° C. to crosslink and gel the composition for crosslinked molding in the mold, thereby providing a crosslinked molding.

The crosslinked molding thus prepared showed no sticking property at the gel portion, was flexible and rich in elasticity as in Example 11, but the product was not adhered to the polyester substrate and was easily peeled off.

COMPARATIVE EXAMPLE 2

A toluene solution of acrylated modified liquid polybutadiene was coated on one surface of a polyester film of 25 μm in thickness and dried at 40° C. for 5 hours to evaporate off the solvent, thereby forming a primer composition layer of 30 μm in thickness. The surface of the composition for crosslinked molding degassed as in Example 11 was covered with the above-obtained film and heat-treated at 120° C. to crosslink and gel the composition for crosslinked molding in the mold, thereby providing a crosslinked molding.

The crosslinked molding thus prepared showed no sticking property at the gel portion, was flexible and rich in elasticity, and strongly adhered to the primer composition. However, the adhesive property between the primer composition and the polyester film was poor and the primer composition was easily peeled off.

COMPARATIVE EXAMPLE 3

A toluene/methyl ethyl ketone solution of a polyester resin was coated on one surface of a polyester film of 25 μm in thickness and dried at 40° C. for 5 hours to evaporate off the solvent, thereby forming a primer composition layer of 30 μm in thickness. The surface of the composition for crosslinked molding degassed as in Example 11 was covered with the film and heat-treated at 120° C. to crosslink and gel the composition for crosslinked molding in the mold, thereby providing a crosslinked molding.

The crosslinked molding thus prepared showed no sticking property at the gel portion, was flexible and rich in elasticity. However, the crosslinked molding did not adhere to the primer composition and was easily peeled off.

EXAMPLE 14

After cooling a viscous solution obtained by the same manner as in Example 2 to a temperature below 40° C., 4 g of lauroyl peroxide was added thereto, and after sufficiently stirring the mixture, the mixture was flow-cast in a mold (7 cm×22 cm×5 cm) followed by degassing.

Figure 4:
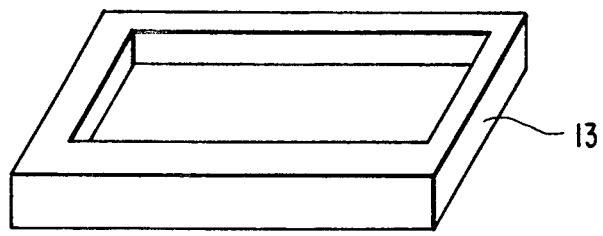
FIG. 4 is a slant view showing an example of a fixing member for fixing an ultrasonic probe.

On the other hand, a polyester nonwoven fabric (basis weight 50 g/m$^2$) was adhered to a picture frame-form acrylic resin plate (outer size: 5 cm×20 cm×2 cm, inner size: 4 cm×15 cm×2 cm) as shown in FIG. 4 using a cyano acrylate series adhesive.

After finishing degassing of the above viscous solution, the acrylic resin plate was immersed in the viscous solution and heat-treated at 100° C. under a nitrogen gas atmosphere to crosslink and gel the solution, thereby providing a crosslinked molding.

The crosslinked molding did not have a sticking property and was flexible and rich in elasticity. The crosslinked molding had been strongly adhered to the substrate and when they were allowed to stand for one month, the crosslinked molding was not peeled off.

Figure 5:
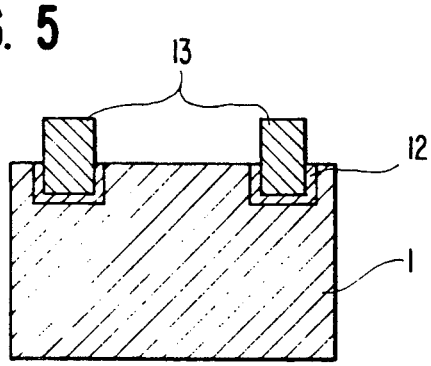
FIG. 5 is a cross-sectional view showing the case of integrating the fixing member shown in FIG. 4 and the sound medium of the present invenion in a body.

By the same manner as described above, an ultrasonic coupler integrated with an ultrasonic probe-fixing member (holder) in one body as shown in FIG. 5 was prepared. When the ultrasonic coupler was used for an image diagonsis, the operability was good and the gelatinous high molecular weight material layer as a sound transmitting medium was not peeled off from the holder.

As described above, since the sound medium of the present invention has the above-described constitution, the sound medium is excellent in a shape retention property, flexibility and a proper elasticity, and the oily material contained therein does not cause blooming with the passage of time.

Since the sound medium scarcely absorbs water, the medium is not influenced by moisture in the air, a specific sealing package is unnecessary, and the quality is stable. Furthermore, since the sound medium has sound characteristics close to the living body, when the sound medium is used for ultrasonic diagonosis and ultrasonic medical treatment, the medium gives an excellent effect.

While the invention has been described in detail and with reference to specific embodiments thereof, it will be apparent to one skilled in the art that various changes and modifications can be made therein without departing from the spirits and scope thereof.

We claim:

1. A crosslinked molding, wherein said molding comprises a molded composition comprising:
   a rubbery elastic body, wherein said rubbery elastic body comprises a hydrophobic high molecular weight material having at least one double bond in the molecule, dissolved in
   an oily component,
   and wherein said composition has been crosslinked by the addition of an organic peroxide or by irradiation with radiation.

2. The crosslinked molding of claim 1, wherein the oily component is selected from the group consisting of vegetable oils, mineral oils, ester oils, animal oils and liquid emulsifying agents.

3. The crosslinked molding of claim 1, wherein the oily component is a dibasic acid ester or an organic compound having a benzene ring in the molecule and a specific gravity at 25° C. of at least 0.95.

4. The crosslinked molding of claim 1, wherein the crosslinked molding is formed on one surface of an oil resistant plastic substrate.

5. The crosslinked molding of claim 4, wherein a primer layer comprising:
   (a) a synthetic resin component, wherein said resin component is not dissolved in or swelled by the oily component of the crosslinked molding composition, and
   (b) a rubber component comprising a hydrophobic high molecular weight material having at least one double bond in the molecule, wherein said rubber component is compatible with the synthetic resin component,
   is formed on the surface of said oil resistant plastic substrate.

6. The crosslinked molding of claim 4, wherein a porous layer selected from the group consisting of paper, woven fabric, nonwoven fabric, net, continuous foam and a plane fastener is formed at a part of the surface of the oil resistant plastic substrate and the crosslinked molding is formed on the inside of the porous layer and on the surface thereof.

7. A process for producing a crosslinked molding comprising the steps of:
   (1) pouring a composition for forming the crosslinked molding into a mold having a definite form, or forming a film, wherein said composition comprises:
      a first rubber component comprising a hydrophobic high molecular weight material, wherein said material is compatible with an oily component and has at least one double bond in the molecule dissolved in
      an oily component;
   (2) forming on the surface of an oil resistant plastic substrate a primer layer composition comprising:
      (a) a synthetic resin component, wherein said resin component is not dissolved in or swelled by the oily component of the crosslinked molding composition, and
      (b) a second rubber component comprising a hydrophobic high molecular weight material having at least one double bond in the molecule, wherein said second rubber component is compatible with the synthetic resin component;
   (3) contacting the surface of the composition for forming the crosslinked molding poured into the mold, or formed into a film in step (1), with the primer layer composition on the surface of the oil resistant plastic substrate of step (2); and
   (4) crosslinking each composition contacted in step (3).

8. The process of producing a crosslinked molding of claim 7, wherein the synthetic resin component which is not dissolved in or not swelled with the oily component is a synthetic resin which is the same as or similar to the oil resistant plastic substrate.

9. The process of producing the crosslinked molding of claim 7, wherein the 2nd rubber component is a liquid rubber having a fluidity under the working temperature.

10. The process of producing the crosslinked molding of claim 7, further comprising a step of forming a adhesive layer or a pressure-sensitive adhesive layer on the opposite surface of the substrate to the surface of forming the primer composition layer.

11. An ultrasonic coupler comprising an ultrasonic probe-fixing member adapted to be connected to an ultrasonic probe and the crosslinked molding of claim 1 connected to the fixing member, wherein said ultrasonic coupler is positioned between the ultrasonic wave transmitting and receiving surface of the ultrasonic probe and a testee, and wherein a porous layer is formed at a part of the ultrasonic probe-fixing member and a sound medium comprising the crosslinked molding is formed on the inside of the porous layer and on the surface thereof.

12. The ultrasonic coupler of claim 11, wherein the internal sound velocity at normal temperature is from 1,300 to 1,600 m/sec., the sound impedance is from 1.0 to $1.7 \times 10^6$ kg/m²·second, and the attenuation ratio is from 0 to 3.0 dB/cm·MHz.

13. The ultrasonic coupler of claim 11, wherein the ultrasonic coupler contains at least one of inorganic fillers, plastic beads, and fibers, as an attenuation controlling agent.

14. The ultrasonic coupler of claim 11, wherein the surface of the crosslinked molding is covered with an oil resistant plastic film.

15. The ultrasonic coupler of claim 14, wherein a reinforcing material for the crosslinked molding is formed adjacent to the crosslinked molding or is partially or wholly embedded in the crosslinked molding.

16. The ultrasonic coupler of claim 15, wherein the reinforcing material is formed in a position which is outside of the path of the ultrasonic pulses transmitted from the ultrasonic probe.

17. The ultrasonic coupler of claim 16, wherein the reinforcing material is formed in a perpendicular direction to an ultrasonic wave transmitting and receiving plane of the ultrasonic probe.

18. The ultrasonic coupler of claim 15, wherein the reinforcing material is immersed in the gel composition solution for forming the crosslinked molding before the gel composition solution is gelled, and wherein the resulting ultrasonic coupler integrates the crosslinked molding and the reinforcing material in one body.

19. The ultrasonic coupler of claim 15, wherein the reinforcing material comprises a flexible material selected from a net, a plastic film, a paper, a nonwoven fabric, and a woven fabric.

20. The ultrasonic coupler of claim 15, wherein the reinforcing material has an uneven lower edge.

* * * * *